United States Patent [19]

Oreopoulos et al.

[11] Patent Number: 4,508,367

[45] Date of Patent: Apr. 2, 1985

[54] CONNECTOR

[76] Inventors: Dimitrios G. Oreopoulos, 10 Ladywood Dr., Rexdale, Ontario; Gabor Zellerman, deceased, late of Ottawa, both of Canada; by Robert G. Price, administrator, 1801 - 20 Driveway, Box 1565, Stn. B, Ottawa, Ontario, Canada, K1P 5R5

[21] Appl. No.: 442,457

[22] Filed: Nov. 17, 1982

Related U.S. Application Data

[63] Continuation-in-part of Ser. No. 111,264, Jan. 11, 1980, abandoned.

[30] Foreign Application Priority Data

Jan. 15, 1979 [CA] Canada .................................. 319367

[51] Int. Cl.³ ............................................. F16L 35/00
[52] U.S. Cl. .......................................... 285/3; 285/24; 285/331; 285/423; 285/DIG. 2
[58] Field of Search ................ 285/3, 4, DIG. 2, 331, 285/260, 423, 110, 133 R, 138, 24, 27

[56] References Cited

U.S. PATENT DOCUMENTS

| | | | |
|---|---|---|---|
| 3,521,913 | 7/1970 | Verhein et al. | 285/110 X |
| 3,768,476 | 10/1973 | Raitto | 285/331 X |
| 3,976,311 | 8/1976 | Spendlove | 285/DIG. 2 |
| 3,986,508 | 10/1976 | Barrington | 285/3 |
| 4,004,614 | 1/1977 | Malkal | 285/DIG. 2 |
| 4,030,494 | 6/1977 | Tenczar | 285/3 X |
| 4,187,846 | 2/1980 | Luluchi | 285/3 |
| 4,194,765 | 3/1980 | Reddy | 285/423 |
| 4,201,406 | 5/1980 | Dennehey | 285/27 X |
| 4,225,162 | 9/1980 | Doh | 285/331 |

Primary Examiner—Dave W. Arola
Attorney, Agent, or Firm—Fetherstonhaugh & Co.

[57] ABSTRACT

The invention is a coupler for interconnecting the ends of two fluid conduits wherein the connectors are each mounted inwardly of the open end of respective cupped members; the cupped members telescope one over the other and one of them has a flared end to assist in the initial alignment of the telescoping action. The connectors connect with each other to establish fluid flow as the cupped members are telescoped together.

10 Claims, 7 Drawing Figures

CONNECTOR

The application is a continuation-in-part application of Application Ser. No. 06/111,264 filed Jan. 11, 1980, and now abandoned.

FIELD OF INVENTION

This invention relates to a fluid flow coupler that is useful in the practice of peritoneal dialysis for persons who have suffered kidney failure.

PRIOR ART

Continuous ambulatory peritoneal dialysis (CAPD) is a system of dialysis wherein a quantity of dialysate is admitted to the peritoneal cavity of a patient, permitted to remain there for a period of about six hours within which it performs its dialysis function and then drained from the peritoneal cavity. The step of admitting fresh dialysate to the peritoneal cavity is repeated after drainage. About two liters of dialysate is usually admitted to the cavity. A patient on the system is required to change the dialysate four or five times a day, six or seven days a week.

The dialysate is preferably supplied to the patient from a plastic container and provision must be made for connecting and disconnecting the container to a tube through which flow can take place to or from the patient.

With the peritoneal dialysate technique, peritonitis is a danger and extreme care must be exercised at the point of connection of the container and the tube to ensure that the dialysate solution does not become contaminated.

Quite often, persons using the system are not themselves in the best of health and, therefore, not capable of putting forth a good effort to make an efficient connection. They tend to fumble and to handle the parts of the connector more than is desirable and this can result in dialysate contamination and peritonitis.

It is, therefore, important to provide a coupler for connecting a tube to an opening in the dialysate container that can be manipulated and aligned with a minimum of effort and in a way wherein the connected parts through which dialysate flow will take place are not likely to be touched by the hands of the person making the connection.

SUMMARY OF INVENTION

A coupler, according to this invention, comprises a first part with a first cupped member having an open end, an exterior cylindrical wall extending rearwardly of the open end and a flow opening extending through the bottom thereof, a second part with a second cupped member having an open end, an interior cylindrical wall extending from the open end and a flow opening extending through the bottom thereof, the diameter of the interior cylindrical wall of the second cupped member being slideable over the diameter of the exterior wall of the first cupped member whereby the two cupped members can be telescoped with respect to each other along an axis common to the cylindrical axis of their said respective cylindrical walls when the cylindrical axes of their respective cylindrical walls are aligned and their open ends are opposed whereby said parts are telescopable with respect to each other, a connector for each of said cupped members for joining fluid flow between the flow openings of said cupped members, said connector in each of said cupped members being spaced inwardly from the open end of its respective cupped member, said connectors being aligned in their respective cupped members and adapted to connect together in fluid flow relation within the first cupped member as the cupped members are telescoped together, the inside cylindrical wall of said second cupped member being flared outwardly adjacent its open end to guide said cupped members into axial alignment for telescoping together, the said cupped members when fully telescoped being adapted to maintain said connectors connected in fluid flow relation.

PREFERRED EMBODIMENT

Figure 1:
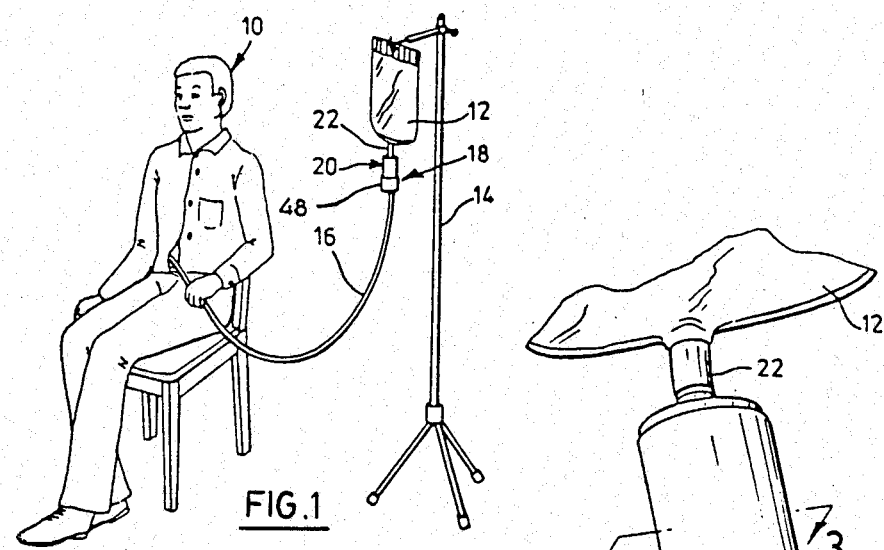
FIG. 1 is an illustration of a patient sitting while connected to a bag of dialysate.

In FIG. 1 of the drawings, a patient 10 is shown receiving dialysate from a plastic bag 12 that is suspended on a stand 14. The dialysate flows by gravity from the bag through the plastic tube 16 which is connected to a catheter permanently implanted in the patient's peritoneal cavity. The tube 16 is connected to the bag by means of a coupler generally indicated by the numeral 18. One part 20 of the coupler has a skirted base and the other part 48 of the coupler has a skirted base and interconnection of the bag to the tube is made by joining the two parts of the coupler. A manually releasable clip 26 is mounted on the tube 16 and can be manipulated to pinch the tube to stop flow therethrough in the position illustrated in FIG. 4. Alternatively, it can be released to permit flow through the tube. The construction and operation of the clip 26 is well known and will not be referred to in detail in the specification.

Figure 3:
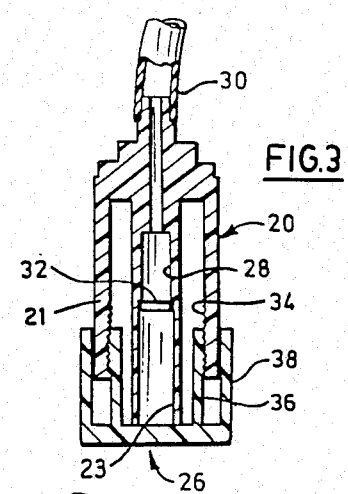
FIG. 3 is a sectional illustration of the cupped member of FIG. 2 with its cap applied thereto.

In use, the bag of dialysate 12 with its coupler part 20 is supplied to the patient with a cap 26 as illustrated in the sectional view which is FIG. 3 of the drawings.

It will be noted that coupler part 20 has a skirt 21 that forms a skirt for the cupped member 23. It also has a tubular connector 28 that terminates at the membrane 32 that extends thereacross and seals the contents of the container 12 in the container until broken as will be explained later. The inside of the outside skirt 21 of the connector part 20 is threaded as at 34 to threadedly receive a wall 36 that is spaced inwardly from the outside wall 38 of cap 26.

Thus, the bag of dialysate 12 is sealed by the membrane 32 and the connector part 20 has a cap that is threaded thereon and that has a skirt 38 that extends over and protects the free end of the outer surface of the outer wall of the connector part from undue handling contamination.

The whole container with its cap, as illustrated in FIG. 3, can be manufactured and shipped in an outer soft plastic bag which further maintains sterility of the unit until required for use. These units can be shipped in sterile condition and maintained in sterile condition until removed from their outer plastic bag container in accordance with known handling technique.

The patient normally carries the tube 16 in a rolled up condition contained in a body pouch. The connector part 48 has a cupped member 24 that is permanently attached to the end of the tube 16. Connector part 48 has a tubular connector 40 extending therethrough and axially thereof and it connects with the tube 16 as at 42.

Under normal conditions of use, the inside of the cupped member 24 must be maintained sterile and when not connected to a container 12, a cap 42 is threaded over the threaded shoulder 44 of the cupped member 24 and the enclosed space is filled with a sterilizing solution, such as Providin. The clip 26 is closed to prevent the Providin from travelling through the tube to the patient. Connector 48 has a skirt that extends over the free end of the cap 42. A guide pin 50 extends substantially beyond the cap and engages in the tubular connector 40 to ensure proper alignment of the cap over the cupped member 24 as the cap member and cupped member are connected and disconnected. In use, one usually puts a slight excess of sterilizing solution into the cap so that the excess is forced out through the loose fitting threaded connection between the cap and the cupped member to ensure sterility of the abutting walls of the connected parts.

The cupped member 24 of connector part 48 is flared outwardly to assist its axial alignment with the outside wall of cupped member 23 for telescoping together. This assistance in alignment is of very significant practical importance because it provides a facility of handling without contamination in the case of persons who are not in the best of health. It makes it easy for them to make the interconnection without significant danger of touching the sterile connectors of the unit. In use, they grip the cupped members by their outside walls only.

Figure 4:
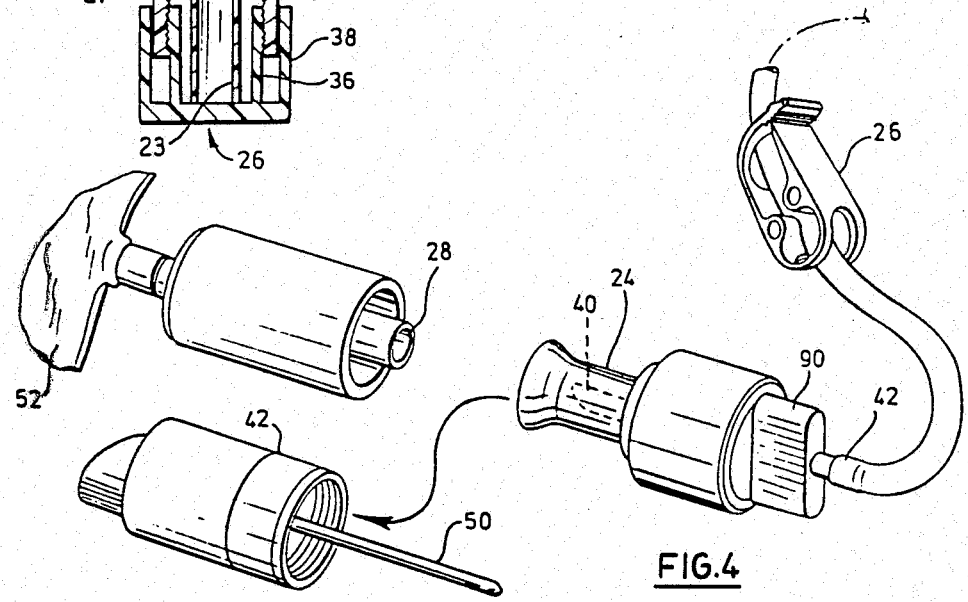
FIG. 4 is an illustration of two cupped members of a connector together with a cap that can be applied to one of the cupped members to maintain it in a sterile condition.

In use, a patient desiring to drain dialysate solution in the peritoneal cavity takes the connector part 48 and removes the cap 42 as indicated in FIG. 4 of the drawings. He handles the part only by its outside wall. He then connects the connector 40 an empty dialysate bag 52 which is mounted at an elevation lower than the peritoneal cavity.

Figure 5:
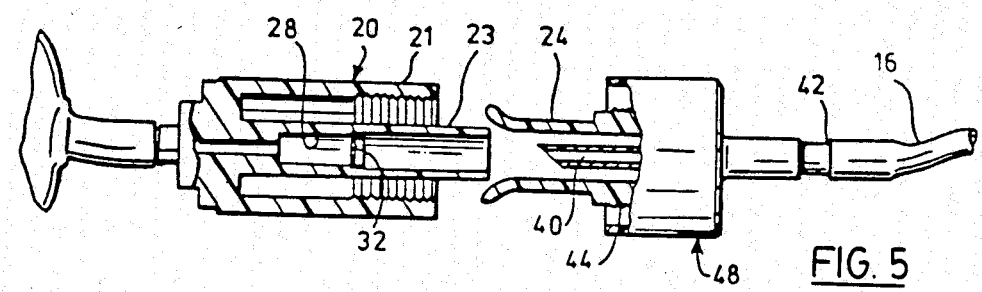
FIG. 5 is an illustration of the cupped members of a coupler about to be interconnected.
Figure 6:
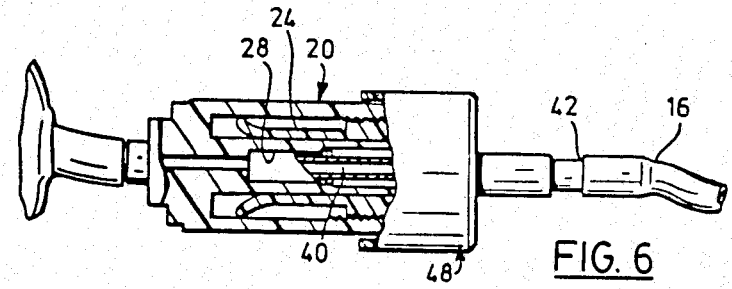
FIG. 6 is in illustration of the cupped members of the coupler of FIG. 5 in connected position.
Figure 7:
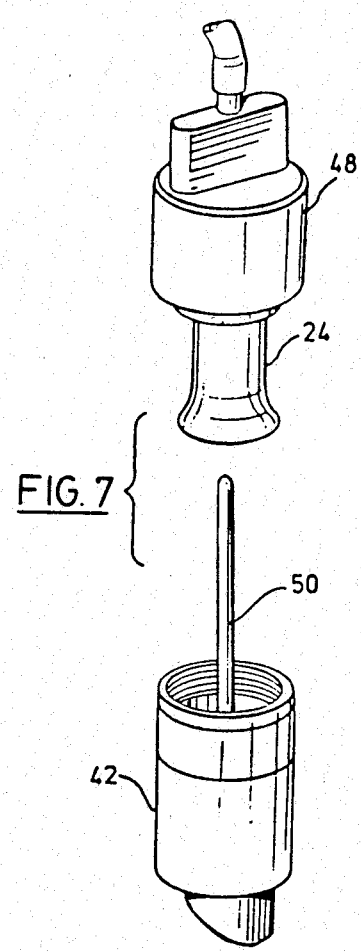
FIG. 7 shows a cupped member of the coupler illustrated in FIGS. 5 and 6 with its cap about to be applied thereto.

FIG. 5 illustrates the bringing together of the connector parts 20 and 48 to unite the connectors 28 and 40. It will be noted that the connectors 28 and 40 being aligned in their respective cupped members, telescoped together in fluid-tight relation within the space defined by the cupped members as the cupped members are telescoped together. FIG. 6 illustrates the cupped members fully telescoped together with the connectors 28 and 40 in fluid-tight relation. The final stages of the interconnection are achieved by screw-threading the connector parts together and it will be noted that the threaded barrel portion 44 of connector 48 threadedly engages with the threaded surface 34 of connector 20 to give a good mechanical advantage to the telescoping action as the membrane 32 of the connector 28 is broken.

It will be noted that connector 40 pierces the membrane 32 of connector 28 and thereby establishes a fluid-tight connection within the cupped members.

It is not necessary in the embodiment of the invention illustrated that the end of spiked connector 40 should be a fluid-tight fit with the walls of the connector 28 because the fluid-tight connection is achieved at the membrane 32.

The connector 40 is spaced inwardly of the wall of the cupped member 23 as the cupped members are brought together and separated. The telescoping cupped members guide the connectors towards each other in a manner that the connector 40 cannot become contaminated because it does not touch anything as it is moved to and from the connecting position. Connector 28 is, of course, well within the cupped member and it is also relatively inaccessible for contamination. The connectors are each spaced inwardly of their respective cupped members.

The patient then removes clip 26 from the tube 16 and the solution drains from the peritoneal cavity to the bag 12.

When drainage has been completed, the connector parts are separated and the cupped member 24 with its connector 40 is connected to a cupped member 23 with its connector 28 on a full bag of fresh dialysate. The connection is made in the same manner as just explained. Preferably, the cap 42 with a quantity of sterilizing solution is applied to the cupped member 24 and then removed prior to connection to the full bag of dialysate but this is not necessary if care is taken.

The connector part 20 can easily be manipulated by handling its outside surface near its base. Similarly, the cupped member 24 can be handled near its base by gripping the skirt 48 thereof.

Figure 2:
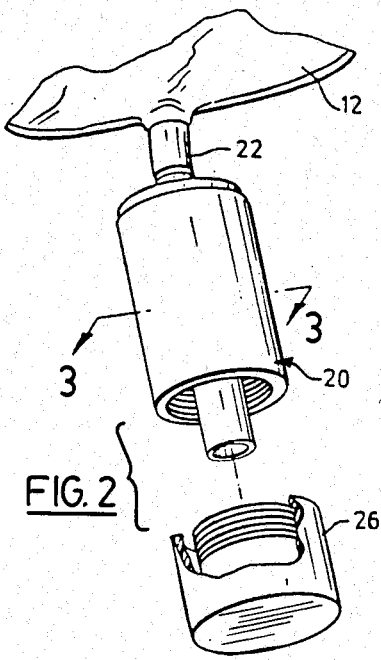
FIG. 2 is an illustration of a cupped member for a coupler according to this invention mounted at the neck end of a container for liquid with a cap therefor.

In use, one of the cupped members will most likely be connected to the dialysate bag as illustrated in FIG. 2 at the time the bag is filled. It will be disposed of as the contents are drained in most cases.

After a bag of dialysate has been drained into the peritoneal cavity of the patient, the patient will, of course, disconnect the connector part that is attached to his catheter tube 16 and apply its cap to maintain its sterility as indicated above. The empty dialysate bag can be stored and used to collect the drainage. In such a case, a cap should be applied to the cupped member while it is not in use to maintain sterility of the connector during the interval. Alternatively, a fresh empty bag with a cupped member that is maintained in sterile packaging can be used for drainage.

When the connector is used to drain dialysate from the patient and the same bag that supplied the dialysate is used to take the drainage, the membrane 32 of the connector 28 will have been broken previously to the making of the drainage connection. In this particular case, the connection between the connectors may not be fluid-tight because the membrane has been previously broken. This, however, is not of any real concern in the case of a drainage use because the bag is low and there is a very low pressure on the connection.

Embodiments of the invention other than the one illustrated will be apparent to those skilled in the art and it is not intended that the foregoing drawings should be read in a limiting sense.

What I claim as my invention is:

1. A coupler comprising a first part, said first part having a first cupped member integral therewith, said first cupped member having a bottom and an open end, said first cupped member having an exterior cylindrical wall extending rearwardly of the open end to said bottom and formed integral therewith and a flow opening extending through the bottom of said first cupped member;

a second part, said second part having a second cupped member integral therewith, said second cupped member having a bottom and an open end, said second cupped member having an interior cylindrical wall extending from the open end to said bottom and formed integrally therewith and a flow opening extending through the bottom of said second cupped member;

the said interior cylindrical wall of the second cupped member and said exterior cylindrical wall of the first cupped member having diameters for sliding relation with respect to each other whereby the two cupped members can be telescoped with respect to each other along an axis common to the cylindrical axis of their said respective cylindrical walls when the cylindrical axes of their respective cylindrical walls are aligned and their open ends are opposed, whereby said first part and a second part are telescopical with respect to each other;

a connector for each of said cupped members for joining fluid flow between the flow openings of said cupped members, said connector in each of said cupped members being spaced inwardly from the open end of its respective cupped member, said connectors being aligned in their respective cupped members and adapted to connect together in fluid flow relation within the first cupped member as the cupped members are telescoped together;

an end portion of the inside cylindrical wall of said second cupped member being flared outwardly adjacent its open end to a diameter greater than the outside diameter of said first cupped member whereby to cooperate therewith and guide said cupped members into axial alignment when they are telescoped together;

the said cupped members when fully telescoped together to dispose the interior cylindrical wall of the second cupped member and the exterior cylindrical wall of the first cupped member in fully telescoped relation being adapted to cooperate and support said connectors connected in fluid flow relation and means for holding said connectors connected.

2. A coupler as claimed in claim 1 wherein said connector of one of said cupped members comprises a membrane extending thereacross, said connector of the other cupped member comprising a tube, said membrane being breakable by the free end of said tube as said cup members are telescoped together to unite said connectors in said fluid-tight relation, said tubular connector with a membrane being connectable as to container for fluid.

3. A coupler as claimed in claim 2 wherein at least one of said cupped members has a cover for its open end for use when it is not in telescoping relation with the other cupped member, said last mentioned cupped member and its cover being formed with threads and said cover being adapted to threadedly engage therewith to form a fluid chamber that houses its connector.

4. A coupler as claimed in claim 2 wherein said cupped members have covers for their open ends for use when they are not in telescoped relation, at least one of said cupped members and at least one of said covers being threaded, the cover of at least one of said cupped members being adapted to threadedly engage therewith to form a fluid chamber within its respective cupped member.

5. A coupler as claimed in claim 2 being connected to a container for fluid.

6. A coupler as claimed in claim 5 wherein at least one of said cupped members has a cover for its open end for use when it is not in telescoping relation with the other cupped member, said last mentioned cupped member and its cover being formed with threads and said cover being adapted to threadedly engage therewith to form a fluid chamber that houses its connector.

7. A coupler as claimed in claim 5 wherein said cupped members have covers for their open ends for use when they are not in telescoped relation, at least one of said cupped members and at least one of said covers being threaded, the cover of at least one of said cupped members being adapted to threadedly engage therewith to form a fluid chamber within its respective cupped member.

8. A coupler as claimed in claim 1 wherein said means for holding said connectors connected comprises threads formed on said cupped members which are threadedly engageable with each other as they are telescoped together.

9. A coupler as claimed in claim 1 wherein at least one of said cupped members has a cover for its open end for use when it is not in telescoping relation with the other cupped member, said last mentioned cupped member and its cover being formed with threads and said cover being adapted to threadedly engage therewith to form a fluid chamber that houses its connector.

10. A coupler as claimed in claim 1 wherein said cupped members have covers for their open ends for use when they are not in telescoped relation, at least one of said cupped members and at least one of said covers being threaded, the cover of at least one of said cupped members being adapted to threadedly engage therewith to form a fluid chamber within its respective cupped member.

* * * * *